United States Patent
Almogy

(10) Patent No.: US 6,236,454 B1
(45) Date of Patent: May 22, 2001

(54) MULTIPLE BEAM SCANNER FOR AN INSPECTION SYSTEM

(75) Inventor: Gilad Almogy, Givatayim (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 08/990,462

(22) Filed: Dec. 15, 1997

(51) Int. Cl.[7] .................................................. G01N 21/00
(52) U.S. Cl. ........................................ 356/237.3; 356/343
(58) Field of Search .............................. 356/237.3, 237.4, 356/239.8, 343, 376

(56) References Cited

U.S. PATENT DOCUMENTS

| | | | |
|---|---|---|---|
| 3,782,827 | * 1/1974 | Nisenson et al. | 356/376 |
| 4,579,455 | 4/1986 | Levy et al. | 356/394 |
| 4,811,410 | * 3/1989 | Amir et al. | 356/237.5 |
| 5,185,641 | * 2/1993 | Igushi et al. | 356/343 |
| 5,274,434 | * 12/1993 | Morioka et al. | 356/237.4 |
| 5,422,724 | * 6/1995 | Kinney et al. | 356/237.3 |
| 5,463,459 | * 10/1995 | Morioka et al. | 356/237.5 |
| 5,528,360 | 6/1996 | Kohno | 356/237.5 |
| 5,585,916 | * 12/1996 | Miura et al. | 356/237.4 |
| 5,623,340 | * 4/1997 | Yamamoto et al. | 356/237.4 |
| 5,661,561 | * 8/1997 | Wurz et al. | 356/376 |

* cited by examiner

Primary Examiner—Frank G. Font
Assistant Examiner—Zandra V Smith
(74) Attorney, Agent, or Firm—Sughrue, Mion, Zinn, Macpeak & Seas, PLLC

(57) ABSTRACT

An inspection system using dark field imaging includes a multiple beam laser scanning unit and at least one multiple beam dark field imaging unit. The laser scanning unit generates multiple beams which illuminate multiple spots on a surface to be scanned. The imaging unit separately detects light scattered from the multiple spots. The spots are separated by a separation distance which ensures that scattered light from each associated spot are received only by its associated photodetector. Each imaging unit includes collection optics and multiple photodetectors, one per spot. The collection optics and photodetectors are mounted so as to separate the light scattered from the different scan lines. In one embodiment, this separation is provided by arranging the collection optics and photodetectors according to the principles of Scheimpflug imaging.

10 Claims, 5 Drawing Sheets

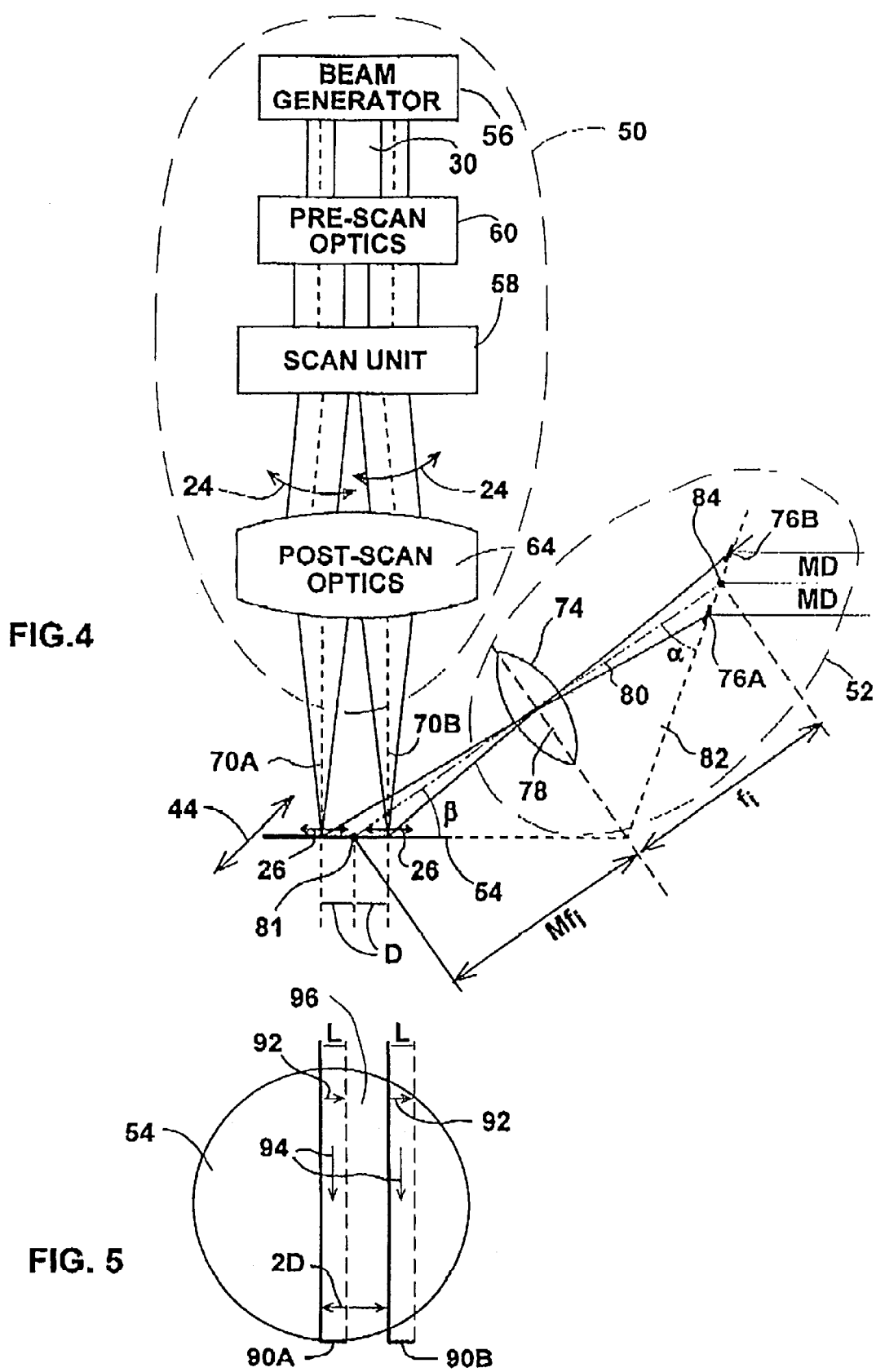

MULTIPLE BEAM SCANNER FOR AN INSPECTION SYSTEM

FIELD OF THE INVENTION

The present invention relates to laser scanning in general and to laser scanning within inspection systems in particular.

BACKGROUND OF THE INVENTION

Laser scanning involves moving a laser beam along a surface to be scanned and can be used for both writing and reading purposes. For example, laser scanning is used for writing in printing systems, where the scanned beam activates spots on a printing medium, and in cutting systems where the scanned beam cuts material. For reading, laser scanning is used in inspection systems and in copiers which use the scanned beam to illuminate consecutive spots of a surface to be viewed or a page to be copied.

FIG. 1, to which reference is now made, schematically illustrates a laser scanning system for printing and a surface 10 of a medium to be activated. The system includes a laser 12, a pre-scan optical system 16, a scan unit 14, and a post-scan optical system 20. The scan unit 14 can be an acousto-optic deflector, a polygon deflector a hologon deflector or an oscillating mirror.

The laser 12 produces a beam 22, the pre-scan optical system 16 provides the scanned beam with the desired optical properties and the scan unit 14 deflects the beam 22 to provide the scanning motion, as indicated by arrow 24. The post-scan optical system 20 focuses the scanned beam on the medium 10, thereby to produce the printing spot, and converts the angular scan of arrow 24 to a linear scan, as indicated by arrow 26.

Due to the action of the scan unit 14, the focused beam scans a portion of the medium 10, as indicated by arrow 26, in one direction, known as the "fast scan direction". The medium 10 typically is moved, as indicated by arrow 26, in a second direction, orthogonal to the fast scan direction. This is generally known as the slow scan direction. The fast and slow scan directions together provide two-dimensional scanning. Alternatively, the scan unit 14 can produce two-dimensional scanning if it includes means for deflecting the beam along a second direction.

The scanning rate (defined as pixels/sec or spots/sec) of any laser scanning system is a function of the velocity of the spot and the size of the spot, both of which are functions of the limitations of the scan unit. The scanning rate is thus limited by the fundamental parameters and quality of the scan unit. It will be appreciated that, for a given pixel or spot size, the scanning rate determines the throughput (e.g. number of pages printed or number of wafers inspected within a given period of time).

It is known to increase the throughput of a laser scanning system for printing by increasing the number of beams being scanned at one time. One such system, with 32 beams, is the ALTA-3500, commercially available from Etec Systems Inc. of California, USA.

FIG. 2, to which reference is now briefly made, schematically shows the system, but with only three beams 30. The multiple beams can be aligned along the fast scan direction, as shown, or along the slow scan direction. A beam generating unit 32, such as multiple lasers or a single laser with multiple beam splitters, produces the multiple beams 30. The multiple beams 30 pass through a system similar to that shown hereinabove for FIG. 1 but whose elements are designed for multiple beams. Thus, the scan unit and pre- and post-optical systems carry similar reference numerals as those of the scanning system of FIG. 1 but are additionally marked with an apostrophe (').

The multiple processed beams, labeled 34, are scanned along the surface of the medium 10, thereby generating multiple parallel scan lines at one time. This typically increases the throughput of the scanning system by the number N of beams used, where an N of two to many hundreds are known.

Laser scanning systems for inspection systems utilize the scanned light for illumination of an article to be inspected by one or more detectors. Such a system is shown schematically in FIG. 3, to which reference is now made. Like the previous scanning systems, it also includes laser 12, scan unit 14, pre-scan optical system 16 and post-scan optical system 20. However, the inspection system also includes multiple light detectors 40 for detecting the shape of features on a surface 42, such as the surface of a semiconductor wafer, from different viewing perspectives. The movement of the surface 42 is indicated by arrow 44.

The scanning elements illuminate the surface 42 from above and the surface 42 scatters the light in many directions, as a function of the optical characteristics of the features thereon. The inspection system of FIG. 3 is a "dark field" inspection system since its detectors 40 collect the light scattered from the surface 42 at an oblique angle $\beta$ which is outside of the convergence angle of the post-scan optical system 20.

The oblique angle $\beta$ varies depending on the type of surface to be inspected and the type of features to be inspected. The light detectors 40 are typically non-imaging detectors, such as a photomultiplier tubes, which measure the changing intensity, over time, of the light impinging upon them. As is known to those skilled in the art, in order to differentiate the light from different pixels on the surface 42, the signal from the photomultiplier tube must be sampled at a rate corresponding to the spot size and to the velocity of the spot on the surface 42. This may be called "temporal resolution".

As in the other scanning systems, the scanning rate of the inspection system of FIG. 3 is a function of the fundamental parameters and the quality of the scan unit 14. Of course, as in other scanning systems, it is desirable to increase the scanning rate of the inspection system. However, an inspection system does not easily lend itself to operating with multiple beams. One reason is that non-imaging detectors do not discern the position from which the light was scattered. Adding other beams would, therefore, cause cross-talk on the detectors caused by the signals from the other spots. Imaging detectors cannot easily be incorporated into a dark field imaging system since, due to oblique incidence angle $\beta$, the collection optics cannot resolve sufficiently small pixels such as is possible with detectors placed at a non-oblique angle.

SUMMARY OF THE INVENTION

An object of the present invention is to provide multiple scanning beams within an inspection system.

There is therefore provided, in accordance with a preferred embodiment of the present invention, an inspection system using at least dark field imaging which includes a multiple beam laser scanning unit and at least one multiple beam dark field imaging unit. The laser scanning unit generates multiple beams which illuminate multiple spots on a surface to be scanned. Each imaging unit collects light from one viewing perspective and separately detects light scattered from the multiple spots.

Moreover, in accordance with a preferred embodiment of the present invention, each imaging unit includes a plurality of photodetectors, at least one per spot, spaced apart from each other and collection optics directing light scattered from each spot to an assigned one of the photodetectors.

In one embodiment, the collection optics and photodetectors are arranged according to the principles of Scheimpflug imaging. For example, the collection optics are mounted so that the longitudinal axis of its thin lens equivalent is at a first non-parallel angle to the surface, the multiple photodetectors are mounted along an image plane of the collection optics and the image plane is at a second non-parallel angle to the longitudinal axis.

Additionally, in accordance with a preferred embodiment of the present invention, the collection optics may include a spatial filter which limits the range of angles of scattered light which are received by the multiple photodetectors. The limiting unit can be an aperture stop. The collection optics can also include wavelength filters and/or polarization filters.

Further, in accordance with a preferred embodiment of the present invention, the multiple beams are separated by a separation distance which ensures that light scattered from each associated spot is received only by its associated photodetector. In one embodiment, the separation distance is generally a multiple K of the length of a scan line less on overlap amount. K can be two. The present invention incorporates other separation distances.

Finally, there is provided an inspection system using dark field imaging which includes a sensor unit which spatially separates between multiple scan lines scanned at generally the same time and which temporally separates pixels within the multiple scan lines.

BRIEF DESCRIPTION OF THE DRAWINGS

The present invention will be understood and appreciated more fully from the following detailed description taken in conjunction with the appended drawings in which:

FIG. 4 is a schematic illustration of a laser scanning system for inspection which uses multiple beams;

FIG. 5 is a schematic illustration of the scanning motions of the system of FIG. 4.

DETAILED DESCRIPTION OF THE PRESENT INVENTION

Figure 1:
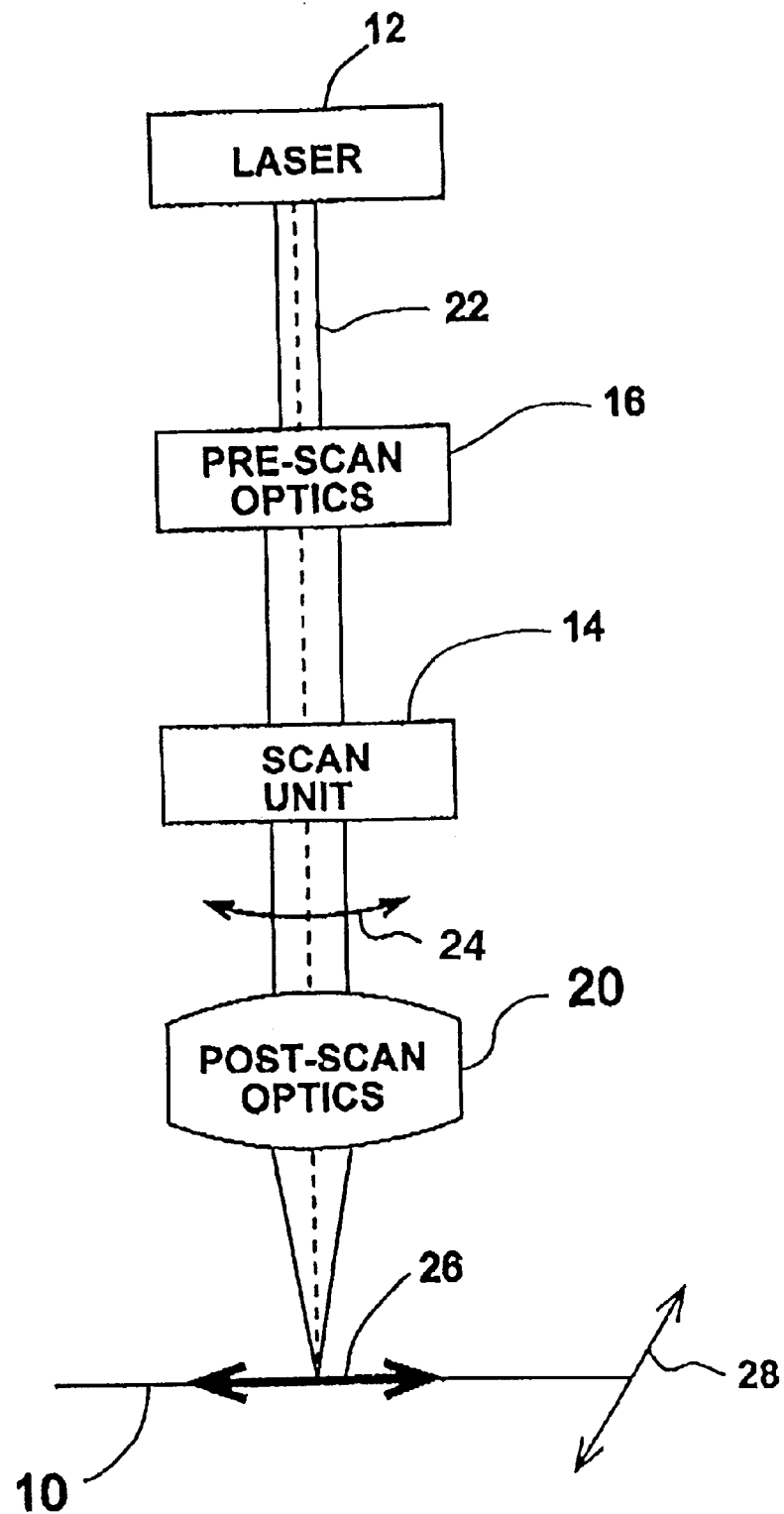
FIG. 1 is a schematic illustration of a prior art laser scanning system for printing.
Figure 2:
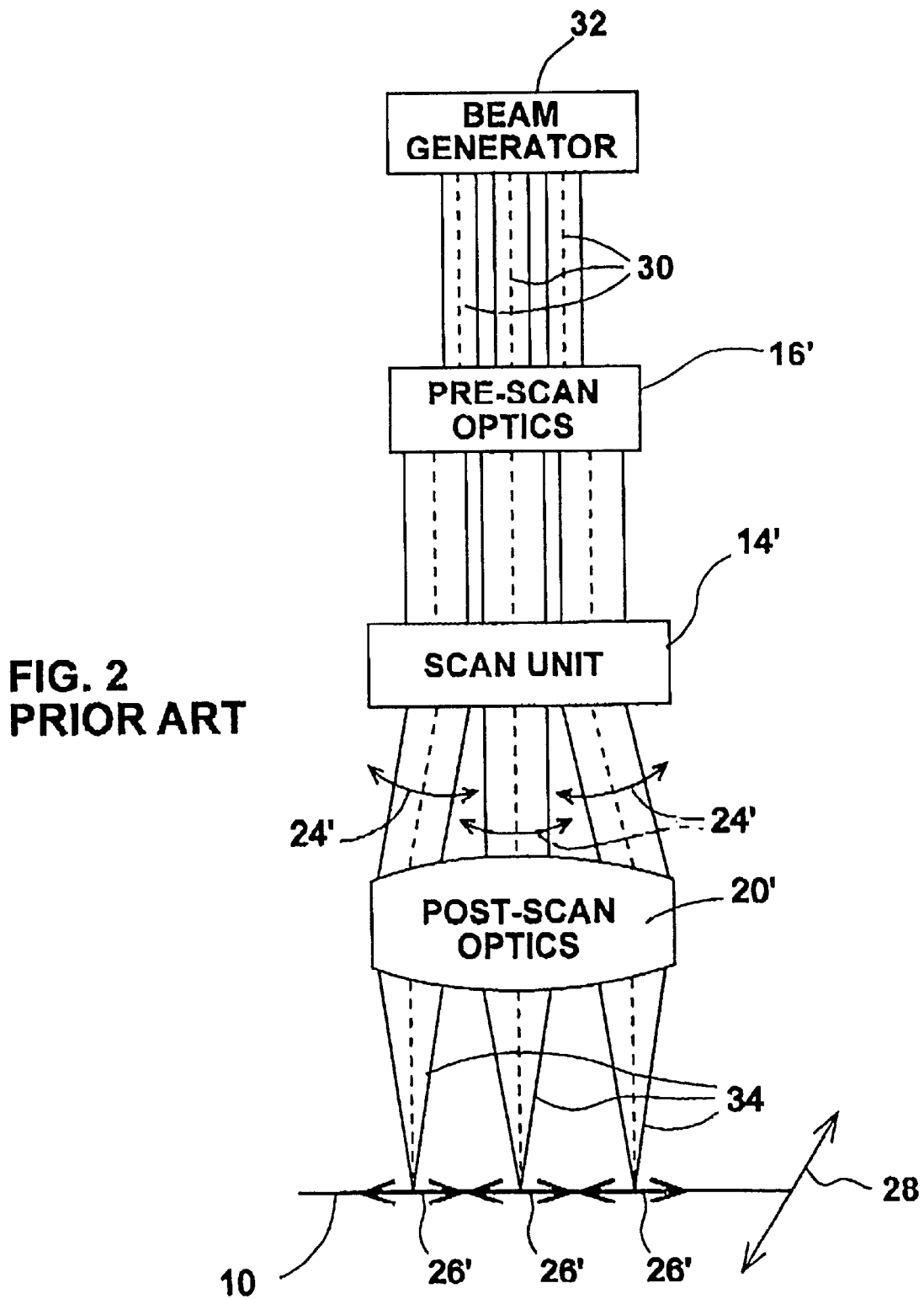
FIG. 2 is a schematic illustration of a prior art laser scanning system for printing which uses multiple beams.
Figure 3:
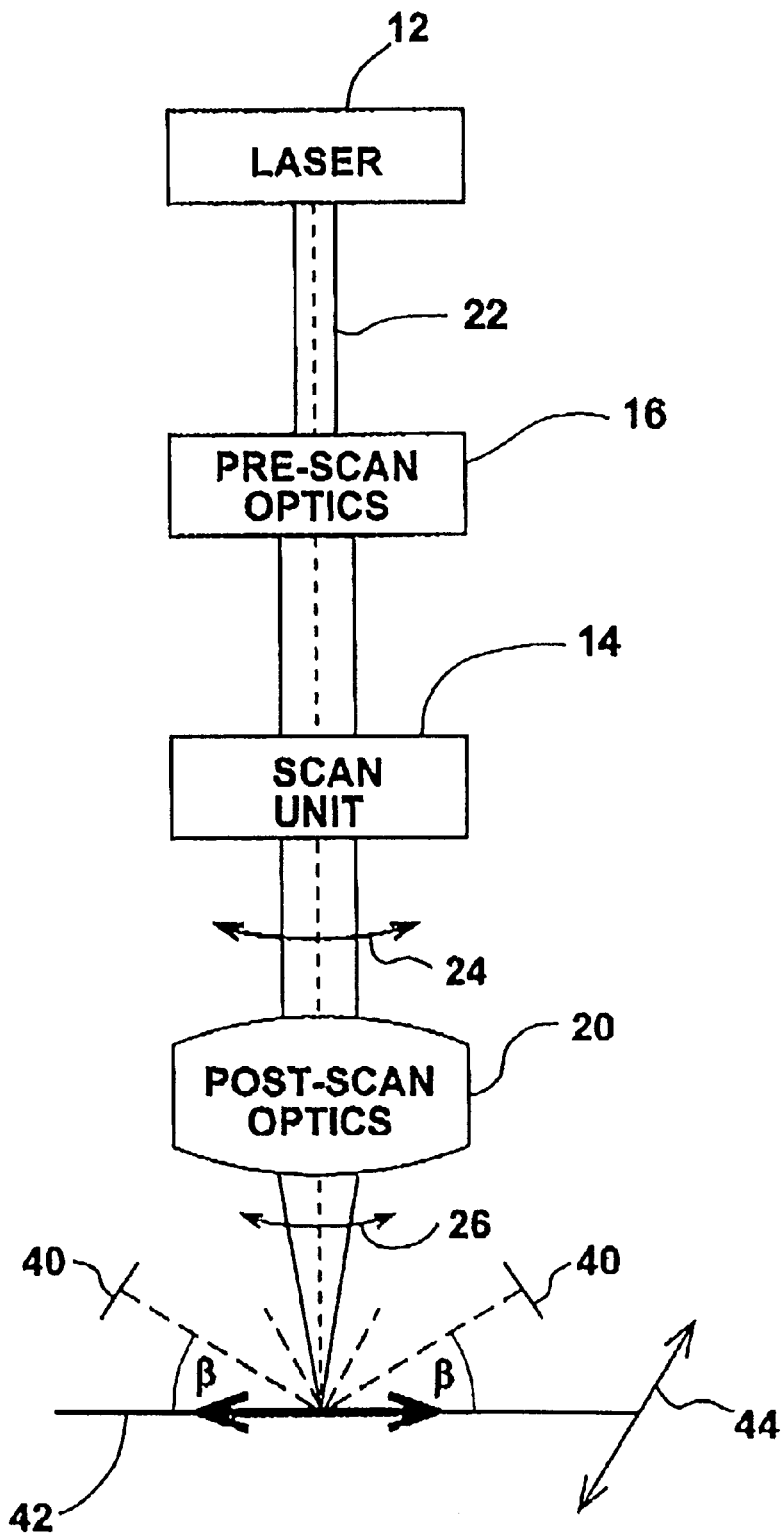
FIG. 3 is a schematic illustration of a prior art laser scanning system for inspection.

Reference is now made to FIGS. 4 and 5 which illustrate the present invention. FIG. 4 illustrates a multiple beam laser scanning system 50 and one multiple beam imaging system 52 per perspective. FIG. 5 illustrates the scan pattern upon a surface to be scanned, such as the surface 54 of a semiconductor wafer.

As in the prior art, the multiple beam laser scanning system 50 comprises a beam generating unit 56, such as multiple lasers or a single laser with multiple beam splitters, one or more scan units 58, a pre-scan optical system 60 and a post-scan optical system 64.

Scanning system 50 scans multiple beams across the surface 54, either one- or two-dimensionally. In the former case, the surface 54 is moved in the second direction.

Two exemplary beams, labeled 70A and 70B, are shown. It will be appreciated that the present invention is operative for two or more beams and that the two shown are for clarity only.

Each multiple beam imaging system 52 comprises collection optics 74 and multiple photodetectors 76, one per spot. FIG. 4 shows one imaging system 52 with two photodetectors, labeled 76A and 76B, which, via collection optics 74, receive the light scattered from the surface 54 when beams 70A and 70B, respectively, impinge thereupon.

Collection optics 74 can be a single lens or multiple optical components, as necessary for the particular application. The discussion hereinbelow will describe the optical qualities of collection optics 74 as though collection optics 74 were a single, thin lens, to be called herein the "collection lens 74". This is known as the "thin lens equivalence".

Collection lens 74 is placed such that its longitudinal axis, labeled 78, is perpendicular to a center line 80 which is at the oblique angle β to the object surface 54. Line 80 extends along angle β from a center point 81 of the scanned beams 70, where center point 81 is defined as the center of the field of view of the collection optics. The collection lens 74 is placed such that center line 80 extends through the center of lens 74.

Surface 54 is the object plane of collection lens 74. However, since the plane of surface 54 is not parallel to the longitudinal axis 78 of collection lens 74, the image plane of collection lens 74 (marked by a dotted line 82) is also not parallel to axis 78. This is known as the "Scheimpflug Condition" and it is described in the book *Handbook of Optics, Vol.* 1, McGraw-Hill, Inc., 1995, sections 1.66 and 1.67, whose disclosure is incorporated herein by reference. According to the Scheimpflug condition, the inclination angle α of the image plane is defined by:

$$\tan \alpha = \frac{\tan \beta}{M}$$

where M is the lateral magnification of imaging system 52.

The photodetectors 76 are placed in the image plane 82 substantially near locations where the scan lines (not shown) of the scanned beams 70 are imaged. If the midpoints of the scan lines scanned by beams 70 are generally at a distance D from center point 81, then centers of photodetectors 76 are generally placed at distances MD from a point 84 where center line 80 intersects with image plane 82.

The distance 2D between the spots must be large enough to ensure that the residual light (as defined by the imaging demands) scattered from one spot does not enter the collection channels of the other spots. Typically, this condition requires the spots to be at least a multiple of the spot width apart.

FIG. 5 shows a wafer surface 54, as seen from the top, and a double scan, of areas 90A and 90B, thereon. Each scan 90 is formed by two orthogonal movements, labeled by arrows 92 and 94. Arrows 92 indicate the fast scan movement of scanned beams 70 as caused by the scan unit 58. Arrows 94 indicate scanning in the slow scan direction.

As discussed hereinabove, the spots must be separated. In the example of FIG. 5, the separation is the length 2L of two scan lines. Therefore, upon the completion of a scan, the two scan areas 90 have been viewed but the area 96 therebetween has not been scanned.

Other separations are possible, such as a separation of half the diameter of the wafer or such as separation within a scan line, and are incorporated in the present invention. If necessary, for system considerations such as the accuracy of a mechanical stage which moves the wafer, the scan lines may overlap. Preferably, the separation between two scan lines being scanned at the same time should be the length of at least two scan lines.

The output of the detectors 76 is processed as in the prior art. That is, the output signal is sampled at a rate corresponding to the spot size and to the velocity of the scanned beams 70 on the surface 54.

It will be appreciated that the present invention temporally separates pixels within each line, as in the prior art, and spatially separates scan lines, using the multiple beams and the multiple photodetectors.

It will further be appreciated that the present invention incorporates all collection lenses 74 which separate the light scattered from the spots so as to identify which light ray came from which spot and not just those which implement the Scheimpflug condition.

Figure 6:
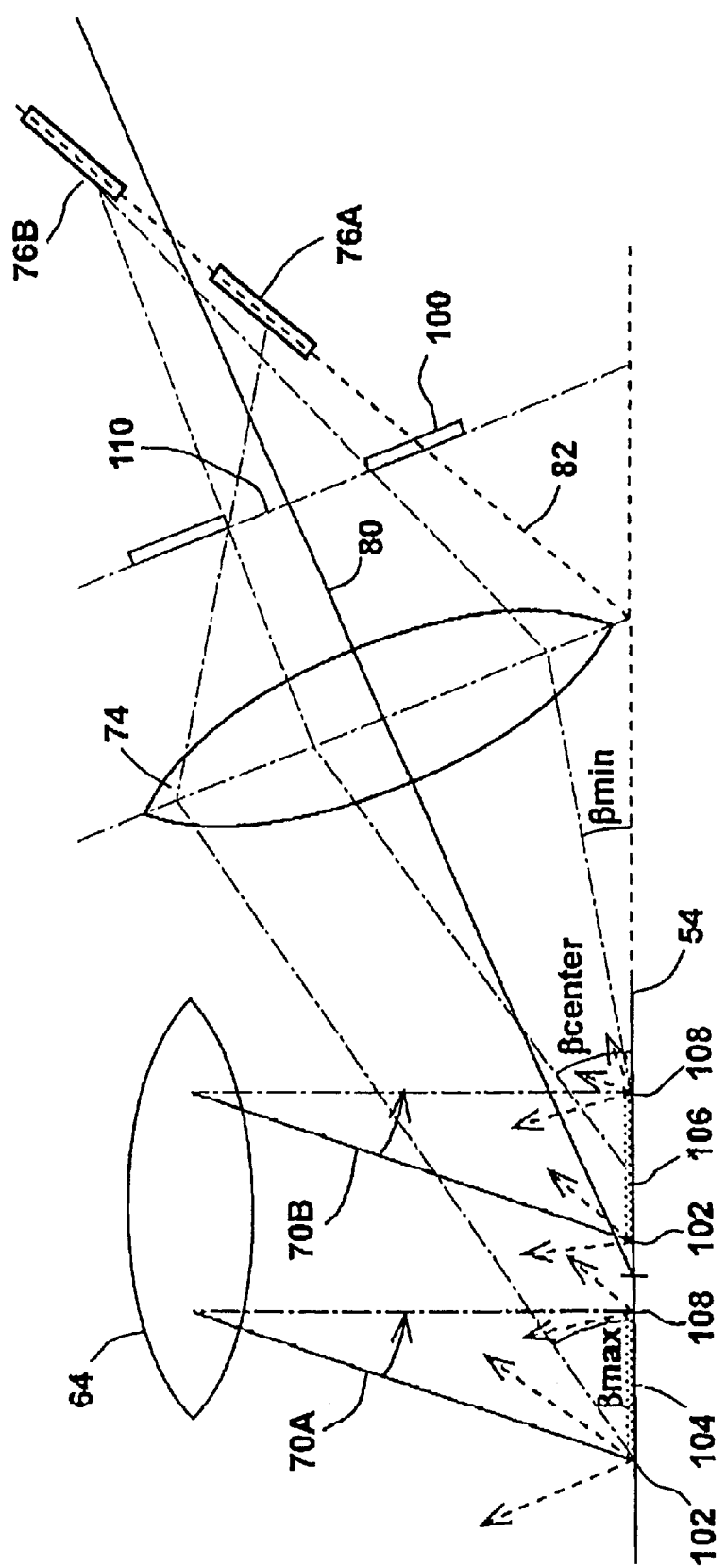
FIG. 6 is a schematic illustration of a spatial filter within the inspection system of FIG. 4.

Reference is now made to FIG. 6 which shows an alternative embodiment of the collection lens of the present invention which limits the collected light to that which is scattered within a predetermined range of angles. This embodiment is useful for inspecting wafers which have a periodic pattern which scatters light in discrete angles. If this known scattered light is filtered out, any remaining scattered light must be due to errors in the wafer. Thus, this embodiment filters the known scattered light in order to view any undesired markings on the wafer.

In this embodiment, the collection optics include a spatial filter 100 in addition to the collection lens 74 and the photodetectors 76. Spatial filter 100 serves to limit the light arriving at the photodetectors 76 to be within a predefined range of angles of scattered light, such that the photodetectors 76 view the same range of angles of scattered light during one scan. Spatial filter 100 can be implemented as an aperture stop or as a mask of any other desired shape so as to spatially filter the incoming light.

FIG. 6 indicates the possible angles of scattered light. The maximum angle of scattered light, labeled $\beta_{max}$, occurs when the leftmost scanning beam 70A is at the beginning point, labeled 102, of its scan line, labeled 104. The minimum angle of scattered light, labeled $\beta_{min}$, occurs when the rightmost scanning beam 70B is at the endpoint, labeled 108, of its scan line 106.

For a magnification of M=1, such as is shown in FIG. 6, the aperture stop 100 is placed one focal length beyond collection lens 74 and the image and object planes are two focal lengths from either side of the collection lens 74. The center of aperture stop 100 is aligned with center line 80 issuing at the center angle $\beta_{center}$. The aperture stop 100 has an aperture 110 which allows only that light which is scattered between $\beta_{max}$ and $\beta_{min}$ to pass through to photodetectors 76.

Other elements, such as polarization filters or wavelength filters, can be utilized to filter the light arriving at the photodetectors 76.

It will be appreciated by persons skilled in the art that the present invention is not limited by what has been particularly shown and described herein above. Rather the scope of the invention is defined by the claims that follow:

What is claimed is:

1. An inspection system using at least dark field imaging, the system comprising:

a multiple beam laser scanning unit generating multiple beams which illuminate spots at the same time on a surface to be scanned, and wherein each beam is different from the others at least in its wavelength or its polarization; and at least one multiple beam dark field imaging unit collecting light from at least one viewing perspective with separate photo-detectors separately detecting light scattered from the multiple spots.

2. An inspection system according to claim 1, wherein chromatic beam-splitters are used to separate the multiple beams.

3. An inspection system according to claim 1, wherein polarizing beam-splitters are used to separate the multiple beams.

4. An inspection system according to claim 1, wherein imaging optics are used to separate the multiple beams and chromatic filters are used to prevent cross-talk between the photo-detectors.

5. An inspection system according to claim 1, wherein imaging optics are used to separate the multiple beams and polarizing filters are used to prevent cross-talk between the photo-detectors.

6. An inspection system using at least dark field imaging, the system comprising:

a multiple beam laser-scanning unit generating multiple beams which illuminate multiple spots at the same time on a surface to be scanned, the spots being separated by a fixed distance in a direction of laser scanning, the fixed distance being a multiple, K, of a length of a scan line less an overlap amount; and at least one multiple beam dark field imaging unit collecting light from at least one viewing perspective and separately detecting light scattered from the multiple spots.

7. The inspection system according to claim 6, wherein said multiple, K, is at least 2.

8. An inspection system using at least dark field imaging, the system comprising:

a source generating a plurality of light beams;

a scanner or scanners simultaneously scanning said light beams over a plurality of respective scan lines; and a sensor system collecting scattered light, spatially separating between the multiple scan lines and temporally separating pixels within said multiple scan lines.

9. An inspection system using at least dark field imaging, the system comprising:

a source generating a plurality of light beams;

a scanner or scanners simultaneously scanning said light beams over a plurality of respective scan lines, said light beams being essentially normal to an inspected surface of an object being scanned; and at least one scattered light collection system which collects light scattered at at least one oblique angle to the inspected surface from each of the light beams onto a respective one of a plurality of sensors.

10. The inspection system of claim 9, wherein said collection system further comprises at least one of: aperture stop, polarization filter, and wavelength filter.

* * * * *